United States Patent [19]

Müller

[11] Patent Number: 4,529,319
[45] Date of Patent: Jul. 16, 1985

[54] METHOD AND APPARATUS FOR THE DETECTION OF THERMO-OPTICAL SIGNALS

[75] Inventor: Gerhard Müller, Aalen-Wasseralfingen, Fed. Rep. of Germany

[73] Assignee: Carl-Zeiss-Stiftung, Heidenheim on the Brenz, Fed. Rep. of Germany

[21] Appl. No.: 444,060

[22] Filed: Nov. 23, 1982

[30] Foreign Application Priority Data

Nov. 25, 1981 [DE] Fed. Rep. of Germany ....... 3146700

[51] Int. Cl.³ .................... G01N 21/01; G01N 21/39
[52] U.S. Cl. .................................. 356/432; 356/435; 374/45
[58] Field of Search ............... 374/45, 124; 356/133, 356/136, 432, 433, 435; 73/655

[56] References Cited

U.S. PATENT DOCUMENTS 3,453,434  7/1969  Takami et al. ............... 356/136 X
4,011,015  3/1977  Baba ............................ 356/136
4,299,494  11/1981  Badoz et al. ................. 374/45 X Primary Examiner—Vincent P. McGraw
Attorney, Agent, or Firm—Stonebraker, Shepard & Stephens

[57] ABSTRACT

Both a method and an apparatus for the detection of thermo-optical signals are disclosed. There is involved a method related to photoacoustic spectroscopy (PAS) in which the heat waves, as a result of the absorption of an amplitude-modulated light beam, are not detected by an acoustic recorder, as in the case of photoacoustic spectroscopy, but rather optically. For this purpose, a second beam of light is conducted over the surface of the specimen and the influence exerted thereon by periodic variations in index of refraction which are dependent on temperature or pressure is measured. For the guiding of the measurement beam a so-called ATR plate known from ATR (attenuated total reflection) spectroscopy is used, it being placed as cover glass over the specimen. Within this plate the measurement light is guided in the vicinity of the critical angle for total reflection at the plate/specimen interface. Changes in index of refraction at the interface as a result of the absorption of the excitation light lead to a detectable modulation of the intensity of the measurement light.

5 Claims, 4 Drawing Figures

METHOD AND APPARATUS FOR THE DETECTION OF THERMO-OPTICAL SIGNALS

BACKGROUND OF THE INVENTION

The present invention relates to a method in which specimens are acted on by a modulated beam of light and the variations in density which are induced thermally as a result of absorption of the light are detected optically at the tempo of the modulation frequency by a second beam of light.

This method is closely related to so-called photoacoustic spectroscopy (PAS) in which the dependence of the absorption of the wavelength of the irradiated light, determined acoustically via variations in density, is investigated. It is furthermore known to produce, on the basis of this method of photoacoustic spectroscopy, an image display of absorbing regions of the specimen within which the exciting beam of light is guided with fixed wavelength over the specimen and the intensity of the detection signal is reported as a function of the locus in the specimen.

For the detection of the variations in density, PAS (photoacoustic spectroscopy) employs a microphone. This microphone may be contained in a pressure-proof housing together with the sample to be examined, and takes up the acoustic waves produced in the gas-filled interior of the housing. Alternatively, the microphone may be cemented directly to the housing and detects the solid-conducted sound which is conducted by the sample itself. Such methods and apparatus are described in Analen der Chemie 47, (1975), page 592 and in British patent application document GB No. 2047896 A, issued 3, Dec. 1980.

Furthermore, from Applied Physics Letters 36 (2), 1980, pages 130–132, a method of detecting variations in density is also known which consists of conducting a beam of light along and slightly above the surface of the specimen to be examined, and detecting the cyclic variations in the angular deflection of the beam as a result of the refractive-index gradients developed over the specimen. By means of this optical method of detection which is based on the so-called mirage effect, sensitivities comparable to those of acoustic detection can be obtained. Since it is not necessary to have a closed specimen chamber and further direct handling of the specimen to be examined (cementing of a piezoelectric sensor) is not necessary, the last-mentioned optical method of detection can be easily handled.

SUMMARY OF THE INVENTION

The object of the present invention is to increase the sensitivity of detection of the last-mentioned method.

This object is achieved by a method and apparatus wherein the specimen is acted upon by a modulated light beam and a second beam of light is guided in a transparent plate applied to the specimen in accordance with the known method of internal total reflection (ATR) in the vicinity of the critical angle and its intensity is measured upon emergence from the plate.

The method of the invention is based on the discovery that even small changes in the difference in refractive indices between the surface of the specimen and a so-called ATR (attenuated total reflection) plate which is placed on it very substantially affect the light-guidance properties of the ATR plate, and that the critical angle for total reflection is thereby changed and thus light losses which are easily detectable photometrically (leaky rays) occur.

The ATR plate is a reflection element which in itself is known for other purposes and consists of a transparent plate of glass which can be provided on the specimen side with a suitable sequence of layers of substances of different indices of refraction. It is used predominantly, but not exclusively, in the infra-red spectral region for investigations by the spectroscopic method of internal total reflection. See German Federal Republic published patent applications Nos. OS 28 37 769, published Mar. 6, 1980, and OS 29 28 419, published Feb. 5, 1981.

In combination with a method of the type indicated above, the use of an ATR plate for the guidance of the second beam of light provides the following advantages: On the one hand the plate can be developed in such a manner that multiple reflections of the beam of light guided in it occur, as a result of which the "photoacoustically" induced light losses are multiplied. On the other hand, the method of the invention is much less insensitive to vibrations since only the intensity of the deflected beam of light and not its angle is to be measured. Both of these factors lead to a considerable increase in the sensitivity of detection.

The second beam of light used for measurement can consist, for instance, of monochromatic light. In such case it is advisable to determine the intensity of the light emerging from the ATR plate by a two-beam method in order to avoid disturbing influences, particularly variations in the intensity of the source of light or stray light from the excitation ray path. However, it is also possible to work on the detection side with "white" light, i.e. light having an extended spectral region. In such case it is advantageous to use one or more detectors which make it possible to measure the spectral displacement of the characteristic line of the ATR plate which acts as a cut-off filter. In the simplest case this requires merely a detector which is sensitized by a suitable filter having a steep slope in the vicinity of the critical wavelength for total reflection.

BRIEF DESCRIPTION OF THE DRAWINGS

Suitable apparatus for carrying out the method will be explained below with reference to the accompanying drawings, wherein.

DESCRIPTION OF THE PREFERRED EMBODIMENTS

Figure 1:
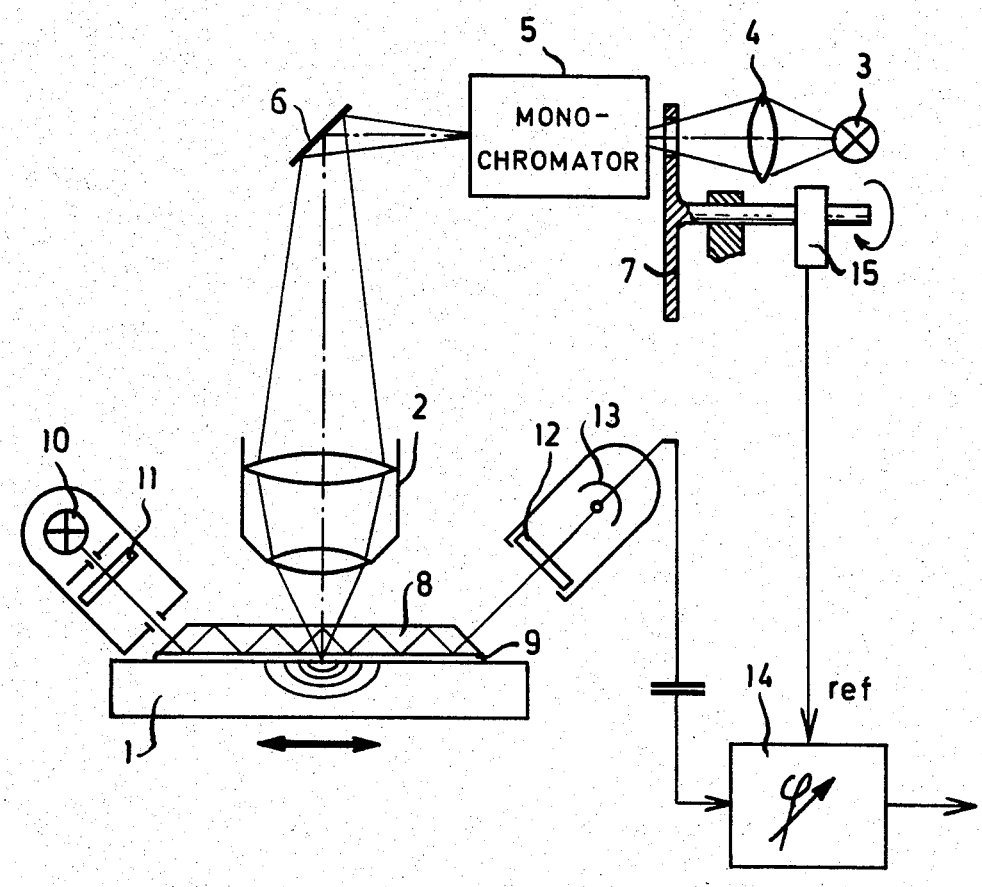
FIG. 1 is a basic diagram of apparatus in accordance with the invention.

The apparatus shown in FIG. 1 can be used both to record thermo-optical spectra and to determine the distribution in space of absorbing regions of a specimen. The surface of a specimen 1 is illuminated through a condenser 2 with monochromatic light. This light is supplied by a lamp 3 and focused by a collector 4 on the inlet of the continuously tunable monochromator 5. Between collector 4 and monochromator 5 there is a chopper 7 which modulates the amplitude of the light.

The outlet-side pin-diaphragm of the monochromator 5 is imaged in reduced size via a mirror 6 onto the surface of the specimen by the condenser 2. Since the specimen 1 is arranged displaceably in the plane of focus of the condenser 2 on a conventional coordinate table (not shown), any desired predetermined regions of the specimen can be excited with the amplitude-modulated monochromatic light spot.

Between the specimen or sample 1 and the condenser 2 there is a so-called ATR plate 8 which is in contact with the surface of the specimen. Onto one of the two beveled ends of the plate 8 there is directed a well-collimated bundle of light coming from the source of light 10 which, after multiple internal total reflection in the plate 8, emerges at the opposite end and is detected by a detector 13.

Figure 2A:
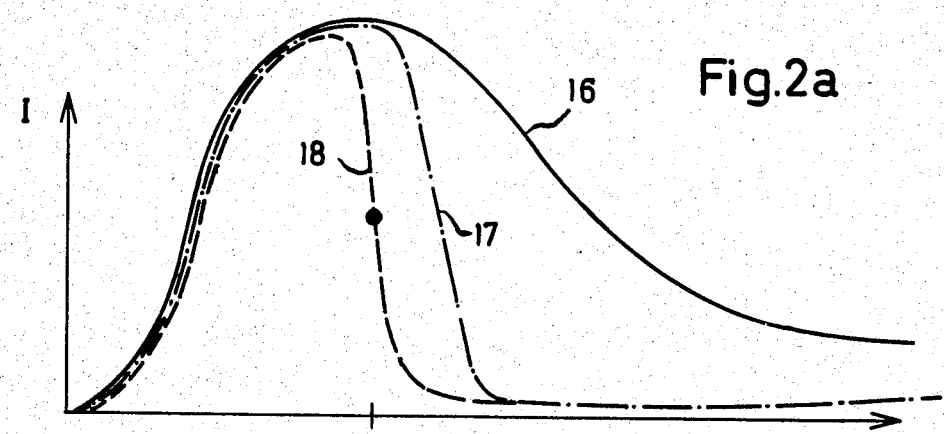
FIG. 2a shows the spectral composition of the "white" light used for the detection, at different points of the ray path.
Figure 2B:
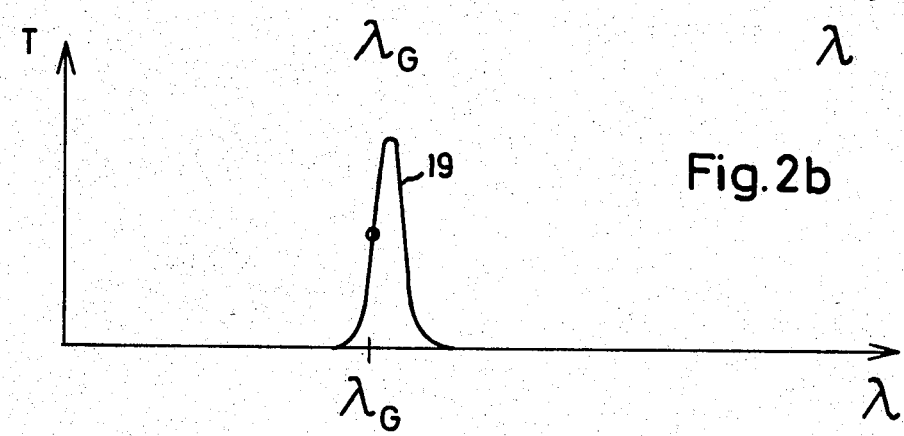
FIG. 2b shows the curve of a filter arranged in front of the photodetector of FIG. 1.

In FIG. 2a the spectral variation of the light emitted by the incandescent bulb 10 is designated by 16. A thermal protection filter 11 (FIG. 1) is opaque to the long-wave part of the light emitted by the lamp 10 so that the light introduced into the plate 8 has the spectral distribution designated in FIG. 2a by the curve 17. A filter 12 may be used in front of the detector 13, if desired.

The introduction of the light into the plate 10 takes place in the vicinity of the critical angle for total reflection at the boundary layer of the specimen 1, coupling layer 9, and plate 8, this angle depending on the indices of refraction of the media in question. Since this limit angle is furthermore dependent on wavelength due to the dispersion of the materials used, a certain amount of spectral dispersion of the light into a part emerging from the plate 8 and a part conducted within the plate 8 takes place, the latter part having approximately the spectral distribution indicated by the curve 18. In FIG. 2a, $\lambda G$ designates the angle-dependent limiting wavelength for total reflection at the plate 8/specimen 1 interface.

As a result of the absorption of the amplitude-modulated light of the source of light 3, small changes of refractive index with the period of the frequency of modulation are formed at the specimen 1/plate 8 interface, these changes effecting a modulation of the limiting wavelength $\lambda G$ of the light conducted within the plate 8. This modulation is converted on the flank of the characteristic curve of the filter 19 as a function of its slope into an amplitude modulation of the light intensity detected by the detector 13. In the phase-sensitive rectifier 14 the alternating-voltage signal given off by the detector 13 is amplified at the frequency of the chopper 7 and can be fed to a recording or storage oscillograph (not shown) which records the intensity of the signal either as a function of the wavelength of the excitation light or as a function of the locus of the specimen.

Figure 3:
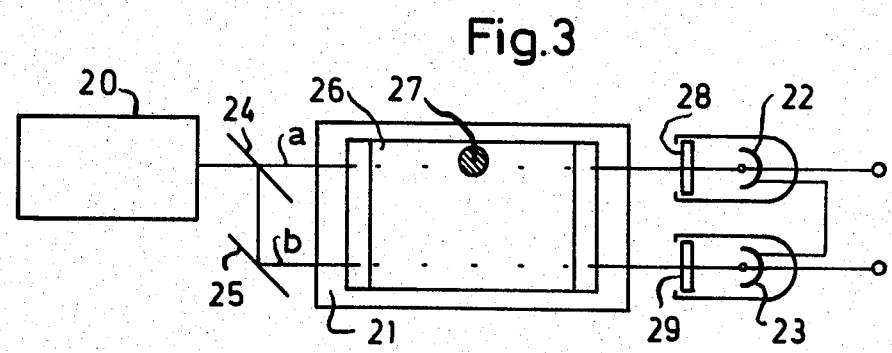
FIG. 3 is a basic diagram of an alternative embodiment of the detection ray path of the apparatus of FIG. 1, shown in top view.

FIG. 3 shows a modified embodiment of the detection channel in top view. As a source of light for the bundle of rays a to be introduced into the ATR plate 26, there is used a continuously tunable laser 20 which, in the same way as the detector 22 used for the detection of the emerging beam, is swingably mounted perpendicular to the surface of the specimen 21, in order to set the critical angle for total reflection. A part of the output intensity of the laser 20 is uncoupled by the divider mirror 24 and conducted by the mirror 25 along a ray path b parallel to the bundle of light a used for detection within the ATR plate 26. For the measurement of this beam of light b, a second detector 23 is used. Filters 28 and 29 are arranged in front of the detectors 22 and 23, the pass regions of the filters being adapted to the wavelength of the light 20. They serve to keep out stray light which is coupled into the plate 26 by the exciting light beam.

The first individual ray a of the laser light used for the detection is guided over the light spot 27 of the exciting light beam and experiences there a slight amplitude modulation as a result of the periodic changes in index of refraction occurring there, while the light beam b passes through the plate 26 substantially unaffected. The difference measurement of the output signals of the two detectors 22 and 23 is the actual measurement signal which has a high signal to noise ratio due to the two-beam method used.

The value of the output signal is dependent on the wavelength of the laser 2 and can be optimalized, referred to the materials used for the specimen and the ATR plate, by tuning the laser. In general, the wavelength of the measurement light should be shorter, the flatter and optically better the surface of the specimen is. The tuning of the wavelength must be effected with continuous adaptation of the angle at which the beams a and b enter into the plate 26, since the critical angle for total reflections which is to be maintained is dependent on the wavelength.

In order to increase the sensitivity of the detection, the ATR plate may be provided on the sample side with a suitable coating, or an optical resonator in the form of a highly refractive plate or layer of liquid which is adapted in its thickness to the wavelength of the radiation of the laser 20 can be arranged between the specimen and the plate. For the dimensioning of such layers reference is had to Applied Optics, Volume 9, No. 9, September 1970, pages 2111–2114.

What is claimed is:

1. Apparatus for measuring thermo-optical response of a rigid specimen, comprising:
  (a) specimen carrier means for holding a rigid specimen;
  (b) a first light source producing a first light beam;
  (c) an optical system for focusing a small spot of light of said first beam on a surface of said specimen;
  (d) scanning means for causing said small spot of light to impinge on different portions of said surface of said specimen;
  (e) modulator means for cyclically changing intensity of said first light beam at a predetermined frequency;
  (f) a second light source producing a second light beam;
  (g) a transparent plate covering said surface of said specimen on which said small spot of light impinges;
  (h) said transparent plate being positioned to receive said second light beam at an entrance location and to guide said second light beam through said plate by internal total reflection from said entrance location to an exit location; and
  (i) detector means for measuring the intensity of said second light beam issuing from said transparent plate at said exit location, thereby to provide a signal indicative of light absorbance characteristics of said specimen.

2. The invention defined in claim 1, characterized by the fact that the plate (8; 26) is a cover glass and bears an evaported coating on the side facing the specimen (1; 21).

3. the invention defined in claim 1, characterized by the fact that an optical resonator is arranged between the specimen and the plate.

4. the invention defined in claim 1, characterized by the fact that the second source of light comprises a tunable laser (20).

5. The invention defined in claim 1, further comprising means for splitting said second light beam into two parts both guided through said transparent plate from respective entrance locations to respective exit locations, one part of said second beam passing in close proximity to said small spot of light and the other part of said second beam being materially spaced from said small spot, said detector means comparing the two parts of said second beam with each other.

* * * * *